United States Patent
Xu et al.

(10) Patent No.: US 11,305,263 B2
(45) Date of Patent: Apr. 19, 2022

(54) METHOD FOR PREPARING A SUPPORTED CARBON CATALYST, SUPPORTED CARBON CATALYST AND USE THEREOF

(71) Applicants: DALIAN INSTITUTE OF CHEMICAL PHYSICS, CHINESE ACADEMY OF SCIENCES, Dalian (CN); FORMOSA PLASTICS CORPORATION, Kaohsiung (CN)

(72) Inventors: Jinming Xu, Dalian (CN); Sisi Fan, Dalian (CN); Yanqiang Huang, Dalian (CN); Tao Zhang, Dalian (CN); Chin Lien Huang, Kaohsiung (CN); Wan Tun Hung, Kaohsiung (CN); Yu Cheng Chen, Kaohsiung (CN); Chien Hui Wu, Kaohsiung (CN); Ya Wen Cheng, Kaohsiung (CN); Ming Hsien Wen, Kaohsiung (CN); Chao Chin Chang, Kaohsiung (CN); Tsao Cheng Huang, Kaohsiung (CN)

(73) Assignees: DALIAN INSTITUTE OF CHEMICAL PHYSICS, CHINESE ACADEMY OF SCIENCES, Dalian (CN); FORMOSA PLASTICS CORPORATION, Kaohsiung (CN)

( * ) Notice: Subject to any disclaimer, the term of this patent is extended or adjusted under 35 U.S.C. 154(b) by 53 days.

(21) Appl. No.: 16/643,953

(22) PCT Filed: Apr. 30, 2019

(86) PCT No.: PCT/CN2019/085315
§ 371 (c)(1),
(2) Date: Mar. 3, 2020

(87) PCT Pub. No.: WO2020/220313
PCT Pub. Date: Nov. 5, 2020

(65) Prior Publication Data
US 2021/0252489 A1    Aug. 19, 2021

(51) Int. Cl.
*B01J 27/20*    (2006.01)
*C07C 17/08*    (2006.01)
(Continued)

(52) U.S. Cl.
CPC .......... *B01J 27/20* (2013.01); *B01J 37/0209* (2013.01); *B01J 37/0219* (2013.01); *C07C 17/08* (2013.01); *C07C 17/25* (2013.01); *C07C 15/46* (2013.01)

(58) Field of Classification Search
CPC .... B01J 27/20; B01J 37/0209; B01J 37/0219; C07C 17/08; C07C 17/25; C07C 15/46
(Continued)

(56) References Cited

U.S. PATENT DOCUMENTS 4,013,573 A * 3/1977 Leikhim ................ C11D 3/162
                                                    510/528
5,139,980 A    8/1992 Nakahara et al.
(Continued)

FOREIGN PATENT DOCUMENTS

CN    104475060 A    4/2015
CN    105217584 A    1/2016
(Continued)

OTHER PUBLICATIONS

International Search Report dated Jan. 17, 2020, in connection with corresponding International Application No. PCT/CN2019/085315 (4 pp., including machine-generated English translation).

*Primary Examiner* — Patricia L. Hailey
(74) *Attorney, Agent, or Firm* — Maier & Maier, PLLC

(57) ABSTRACT

A method for preparing a supported carbon catalyst, the method includes at least the following steps: contacting a gas containing an organic silicon source with a silicon oxide-based material to obtain a precursor; contacting the precursor with a gas containing an organic carbon source to obtain the supported carbon catalyst. The temperature and energy consumption of the chemical vapor deposition of heteroatom-containing carbon material on silica-based materials can be greatly reduced in this method, and the cost of the catalyst can be effectively reduced.

16 Claims, 2 Drawing Sheets

(51) Int. Cl.
    *C07C 17/25*     (2006.01)
    *B01J 37/02*     (2006.01)
    *C07C 15/46*     (2006.01)

(58) Field of Classification Search
    USPC .............................. 502/158, 172, 180, 232
    See application file for complete search history.

(56) References Cited

U.S. PATENT DOCUMENTS

| | | | |
|---|---|---|---|
| 6,251,851 B1 * | 6/2001 | D'Amore | B01J 21/08 502/158 |
| 6,753,287 B1 * | 6/2004 | Weisbeck | B01J 23/52 502/107 |
| 6,995,113 B1 * | 2/2006 | Weisbeck | B01J 23/52 502/243 |
| 8,163,854 B2 * | 4/2012 | Casty | C08F 10/06 526/129 |
| 2003/0134741 A1 * | 7/2003 | Weisbeck | B01J 37/033 502/243 |
| 2012/0071700 A1 * | 3/2012 | Huang | B01J 35/1038 585/259 |
| 2012/0178617 A1 | 7/2012 | Casty et al. | |

FOREIGN PATENT DOCUMENTS

| | | | | |
|---|---|---|---|---|
| CN | 107537587 | * | 1/2018 | .............. B01J 23/42 |
| CN | 109926079 A | | 6/2019 | |

\* cited by examiner

METHOD FOR PREPARING A SUPPORTED CARBON CATALYST, SUPPORTED CARBON CATALYST AND USE THEREOF

FIELD

The present invention relates to a method for preparing a supported carbon catalyst, in particular to a method for controlling the formation of carbon deposit on the surface of porous silicon dioxide.

BACKGROUND

Conventionally, porous carbon materials are generally used as catalyst carriers because of their high specific surface area, furthermore they have good thermal stability and are chemically inert, and thus are widely used as supported metal or metal oxide catalysts. More and more studies have shown that a large number of defect sites can be produced on the surface of the carbon material, and at the same time saturated or unsaturated functional groups containing hetero atoms such as oxygen, nitrogen, phosphorus, sulfur or boron are produced by controlling the preparation method or chemical treatment, which bring the carbon material a certain acid-base property and redox ability and thus the porous carbon material itself has a catalytic activity, for example which can be used in the dehydrohalogenation reaction of halogenated alkane, the dehydrogenation to olefin reaction of alkane and ethylbenzene, etc., the hydrolysis reaction of cellulose and interesterification reaction, etc. Considering the case of a heterogeneous catalyst, the reaction occurs only on the surface of the catalyst, and the inside of the porous carbon material skeleton has little influence on the catalytic activity. Therefore, the nitrogen-containing porous carbon catalyst can be made into a supported type, that is, a thin layer of doped carbon material is covered on the inorganic porous material such as silica to prepare a supported carbon catalyst, which can greatly reduce the cost of catalyst.

Very little carbon deposit can be formed by organics on the surface of relatively pure porous silicon dioxide with less impurity metal ions at a low temperature, so it is very difficult to obtain a certain amount of carbon layer with catalytic activity.

SUMMARY

It is an object of the present invention to overcome the deficiencies of the prior art and to provide a method for preparing a catalyst having carbon doped with other elements on a relatively pure porous silicon dioxide surface with less impurity metal ions.

The temperature and energy consumption of the chemical vapor deposition reaction can be greatly reduced in this method, and the cost of the catalyst can be effectively reduced.

A method for preparing a supported carbon catalyst is provided according to an aspect of the present invention, the method comprises at least the following steps:

(1) contacting a gas containing an organic silicon source with a silicon oxide-based material to obtain a precursor;

(2) contacting the precursor with a gas containing an organic carbon source to obtain the supported carbon catalyst.

Preferably, the organic silicon source in step (1) is at least one selected from the group consisting of a compound with an chemical formula shown in formula I and a compound with an chemical formula shown in formula II:

Wherein $R_1$, $R_2$, $R_3$ and $R_4$ are each independently selected from the group consisting of hydrogen, a $C_1$ to $C_{12}$ hydrocarbyl group, a $C_1$ to $C_{12}$ substituted hydrocarbyl group, a C1 to C5 hydrocarbyloxy group, a $C_1$ to $C_5$ alkylacyloxy group, and a $C_1$ to $C_5$ alkylacyl oxygen, halogen or amino; and At least one of $R_1$, $R_2$, $R_3$ and $R_4$ is a $C_1$ to $C_{12}$ hydrocarbyl group or a $C_1$ to $C_{12}$ substituted hydrocarbyl group; and At least one of $R_1$, $R_2$, $R_3$ and $R_4$ is hydrogen, a $C_1$ to $C_5$ hydrocarbyloxy group, a $C_1$ to $C_5$ alkylacyl oxygen, halogen or amino;

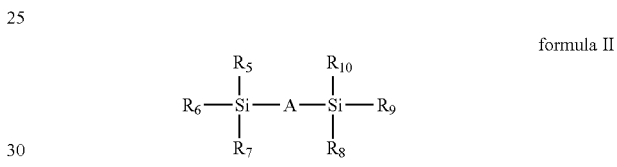

Wherein A is O or NH;

$R_5$, $R_6$, $R_7$, $R_8$, $R_9$ and $R_{10}$ are each independently selected from the group consisting of hydrogen, a $C_1$ to $C_{12}$ hydrocarbyl group, a $C_1$ to $C_{12}$ substituted hydrocarbyl group, a $C_1$ to $C_5$ hydrocarbyloxy group, a $C_1$ to $C_5$ alkylacyloxy group, and a $C_1$ to $C_5$ alkylacyl oxygen, halogen or amino; and At least one of $R_5$, $R_6$ and $R_7$ is a $C_1$ to $C_{12}$ hydrocarbyl group or a $C_1$ to $C_{12}$ substituted hydrocarbyl group; at least one of $R_8$, $R_9$ and $R_{10}$ is a $C_1$ to $C_{12}$ hydrocarbyl group or a $C_1$ to $C_{12}$ substituted hydrocarbyl group.

Optionally, a substituent is contained in the substituted hydrocarbyl group; the substituent is at least one selected from the group consisting of halogen, amino, epoxyethyl, sulfydryl, cyano, isocyanate-N=C=O, and ethylenediamine-$NHC_2H_5NH_2$.

Optionally, the $C_1$ to $C_5$ hydrocarbyloxy group is a $C_1$ to $C_5$ alkoxy group.

Optionally, the organic silicon source in step (1) is least one selected from the group consisting of dichlorodimethylsilane, hexamethyldisiloxane, trimethylchlorosilane, phenyltrichlorosilane, dimethoxydimethylsilane.

Optionally, the gas containing the organic silicon source in step (1) may or may not contain an inactive gas; the inactive gas may be nitrogen or an inert gas, and the inert gas is at least one selected from the group consisting of argon gas, helium gas, and the like.

Those skilled in the art can select the ratio of the inactive gas to the organic silicon source in the gas containing the organic silicon source according to actual needs.

Preferably, the volume percentage of the inactive gas in the gas containing the organic silicon source is ≤99.5%.

Further preferably, in the gas containing the organic silicon source, the volume percentage of the inactive gas is in a range from 10% to 90%.

Optionally, the silicon oxide-based material in step (1) is porous silicon dioxide including silica gel.

Optionally, the gas containing the organic silicon source in step (1) contacts with the silicon oxide-based material at a contact temperature in a range from 100° C. to 500° C. for 0.1 hour to 10 hours.

Preferably, the gas containing the organic silicon source in step (1) contacts with the silicon oxide-based material at a contact temperature in a range from 200° C. to 450° C. for 0.2 hour to 4 hours.

Optionally, the weight hourly space velocity of the organic silicon source in step (2) is in a range from 0.01 $h^{-1}$ to 8 $h^{-1}$.

Preferably, the weight hourly space velocity of the organic silicon source in step (2) is in a range from 0.01 $h^{-1}$ to 1 $h^{-1}$.

Optionally, the mass percentage of the silicon oxide-based material in the precursor is in a range from 80 wt % to 98 wt %.

Optionally, the mass percentage of the silicon oxide-based material in the precursor is in a range from 90 wt % to 97 wt %.

That is, the organic silicon source gas in step (1) is deposited on the surface of the silicon oxide-based material to form a silane, the mass content of silane accounts for 2% to 20% of the mass of the silicon dioxide supported with silane.

The specific kind of the organic carbon source can be selected by those skilled in the art according to actual needs, and organic compounds which can be vapor deposited can be used as the organic carbon source of the present application in principle.

Optionally, the organic carbon source in step (2) is at least one of a $C_1$ to $C_{18}$ organic compound; and the organic compound contains at least one of nitrogen, oxygen, boron, phosphorus, and sulfur.

Optionally, the organic carbon source in step (2) is at least one selected from the group consisting of a $C_1$ to $C_{18}$ oxygen-containing organic compound, a $C_1$ to $C_{18}$ nitrogen-containing organic compound, a $C_1$ to $C_{18}$ boron-containing organic compound and a $C_1$ to $C_{18}$ phosphorus-containing organic compound and a $C_1$ to $C_{18}$ sulfur-containing organic compound.

The oxygen-containing organic compound is at least one selected from the group consisting of alcohol compounds, ether compounds, ester compounds, ketone compounds, phenol compounds, aldehyde compounds, furan compounds, carboxylic acid, and carboxylic ester.

The nitrogen-containing organic compound is at least one selected from the group consisting of amine compounds, nitrile compounds, pyridine compounds, imidazole compounds, pyrrole compounds, nitro compounds, and nitroso compounds.

The boron-containing organic compound is at least one selected from the group consisting of boron alkyl or organic boronic acid.

The phosphorus-containing organic compound is at least one selected from the group consisting of alkylphosphine or organic phosphonic acid.

The sulfur-containing organic compound is at least one selected from the group consisting of thiol compounds, thioether compounds, thiophenol compounds, thiophene compounds, and alkylsulfonic acid compounds.

Preferably, the organic carbon source in step (2) is at least one selected from the group consisting of nitrile compounds, pyridine compounds, organic phosphine compounds, organoboron compounds, thiophene compounds, phenol compounds, and alcohol compounds.

Optionally, the gas containing the organic carbon source in step (2) may or may not contain an inactive gas; the inactive gas may be nitrogen or an inert gas, and the inert gas is at least one selected from the group consisting of argon gas, helium gas, and the like.

Those skilled in the art can select the ratio of the inactive gas to the organic silicon source in the gas containing the organic carbon source according to actual needs.

Preferably, the volume percentage of the inactive gas in the gas containing the organic carbon source is ≤99.5%.

Further preferably, in the gas containing the organic carbon source, the volume percentage of the inactive gas is in a range from 10% to 90%.

Optionally, the precursor in step (2) contacts with the gas containing the organic carbon source at a contact temperature in a range from 500° C. to 1000° C. for 0.1 hour to 10 hours.

Preferably, the precursor in step (2) contacts with the gas containing the organic carbon source at a contact temperature in a range from 600° C. to 900° C. for 0.1 hour to 4 hours.

Optionally, the weight hourly space velocity of the organic carbon source in step (2) is in a range from 0.01 $h^{-1}$ to 8 $h^{-1}$.

Preferably, the weight hourly space velocity of the organic carbon source in step (2) is in a range from 0.1 $h^{-1}$ to 2 $h^{-1}$.

Optionally, the mass percentage of the silicon oxide-based material in the supported carbon catalyst is in a range from 60 wt % to 95 wt %.

Preferably, the mass percentage of the silicon oxide-based material in the supported carbon catalyst is in a range from 75 wt % to 93 wt %.

That is, the mass content of the vapor deposited carbon is in a range from 5% to 40% based on the mass of the catalyst, preferably 7% to 25%.

The silane deposited in step (1) will be pyrolyzed to produce radicals at a high temperature, which induce the organics in step (2) to crack to produce a carbon deposit on the surface of the silica gel, and the amount of deposited carbon can be determined by calculating the weight loss after calcination in air for removing the carbon.

The amount of silane deposited in step (1) can be determined by the weight gain of the silica gel in step (1).

The overall concept of the invention is based on the following scheme:

In step (1), grafting a silane with a hydrocarbonyl group or a substituted hydrocarbonyl group onto the surface of the silica gel, the silane is required to have at least one hydrocarbonyl group or substituted hydrocarbonyl group, and at least one group capable of reacting with the hydroxyl group on the surface of the silica gel such as hydrogen, halogen, alkoxy and the like to graft the silane on the surface of the silica gel.

In step (2), the hydrocarbonyl group or the substituted hydrocarbonyl group in the silane grafted on the surface of the silica gel is pyrolyzed to produce radicals (organic radical and silicon radical) at a high temperature, which induce the organics added in the step (2) to crack to produce a carbon deposit on the surface of the silica gel, so as to promote the deposition of the organics on the surface of the silica gel at a lower temperature.

According to still another aspect of the present application, a supported carbon catalyst prepared according to any of the above methods is provided.

According to still another aspect of the present application, use of the supported carbon catalyst in the dehydrohalogenation of halogenated hydrocarbon, hydrochlorination of acetylene to prepare chloroethylene, the preparation of chloroethylene from acetylene and dichloroethane, the dehydrogenation of alkane to prepare olefin or dehydrogenation of ethylbenzene to prepare styrene is provided.

According to still another aspect of the present application, a method for preparing chloroethylene from 1,2-dichloroethane is provided, wherein a feed gas containing 1,2-dichloroethane is passed through a fixed bed reactor loaded with a catalyst to prepare chloroethylene.

The catalyst is at least one selected from the above supported carbon catalysts.

In the present invention:

$C_1$ to $C_{12}$, $C_1$ to $C_5$, $C_1$ to $C_{18}$, etc. all refer to the number of carbon atoms contained in the group.

For example, "a $C_1$ to $C_{12}$ hydrocarbyl" means a hydrocarbyl group with 1 to 12 carbon atoms.

The "hydrocarbyl group" is a group formed by losing any one hydrogen atom from hydrocarbon compound molecule.

The hydrocarbon compounds include alkane compounds, olefin compounds, alkyne compounds, and aromatic hydrocarbon compounds.

The "substituted hydrocarbyl group" is a group formed by substituting at least one hydrogen atom of hydrocarbyl group with a substituent.

The "alkyl group" is a group formed by losing any one hydrogen atom from alkane compound molecule.

The alkane compound includes a linear alkane, a branched alkane, a cycloalkane, a branched cycloalkane.

The "substituted alkyl group" is a group formed by substituting at least one hydrogen atom of alkyl group with a substituent.

The "hydrocarbyloxy group" means a group formed by losing hydrogen from a hydroxyl group of alcohol compounds.

The "alkylacyloxy group" means a group formed by losing hydrogen from a carboxy group of carboxylic acid compounds.

The "hydrocarbyloxy acyl" means a group formed by losing hydrogen from $HCOOR^a$ of formic acid hydrocarbon ester compounds.

Wherein, Ra is a hydrocarbyl group.

Preferably, Ra is a $C_1$ to $C_5$ alkyl group.

The "amino group" has a formula of $-NR^b_2$, and $R^b$ is hydrogen and/or a hydrocarbyl group.

Preferably, $R^b$ is hydrogen and/or a $C_1$ to $C_5$ alkyl group.

Advantages of the application include, but are not limited to:

(1) the carbon material can be sufficiently supported on the catalyst carrier by firstly grafting the organosilane on the surface of the carrier in the method for preparing a catalyst provided by the present application.

(2) the temperature and energy consumption for the chemical vapor deposition reaction of the hetero atom-containing carbon material on the silicon oxide-based material can be greatly reduced and thus the cost of the catalyst can be effectively reduced according to the method for preparing a catalyst provided by the present application.

(3) the selectivity to chloroethylene is more than 99% using the catalyst prepared by the method described in the present application in the cracking reaction of 1,2-dichloroethane to produce chloroethylene.

DETAILED DESCRIPTION

The method for preparing a supported carbon catalyst comprises the following steps:

(1) depositing an organic silicone source gas on a surface of a porous silicon dioxide as a catalyst carrier by a vapor deposition method;

(2) introducing an organic gas onto the surface of the porous silicon dioxide treated in the step (1) to vapor-deposit the supported carbon on the surface of the porous silicon dioxide.

In the examples, the silica gel pellets with a particle diameter of 2 mm to 4 mm were purchased from Qingdao Ocean Chemical Co., Ltd., and which were colorless and transparent.

Silica gel powder was purchased from Dongying Yiming New Material Co., Ltd., with a particle diameter of 80 mesh to 120 mesh and a color of white;

FNG silica gel was purchased from Qingdao Ocean Chemical Co., Ltd., with a particle diameter of 2 mm to 4 mm and a color of white.

Example 1

The FNG silica gel that washed with hydrochloric acid having a mass concentration of 20% was used as a carrier, the dimethyldichlorosilane was used as an organic silicone source in step (1), and the acetonitrile was used as an organic precursor for vapor-depositing in step (2).

(1) 65 mL of FNG silica gel was put into a quartz tube, the quartz tube was placed in the tube furnace, a nitrogen gas was introduced as a carrier gas and the temperature was raised to 400° C., and then the gas path was switched so that the nitrogen gas carrying the vaporized dichlorodimethylsilane entered into the quartz tube by way of a bubbling device. The vapor deposition process was performed for 2 hours to graft organosilane to obtain a precursor.

In vapor deposition, the flow rate of the nitrogen gas was 100 mL/min; the temperature of the dichlorodimethylsilane bubbler was 25° C.

(2) the gas path was switched so that the nitrogen gas entered into the quartz tube directly not through the bubbling device, and the gas path was switched again after the temperature was raised to 800° C. so that the nitrogen gas carrying vaporized acetonitrile entered into the quartz tube by way of another bubbling device. The chemical vapor deposition process was performed for 2 hours.

In vapor deposition, the flow rate of the nitrogen gas was 100 mL/min; the temperature of the acetonitrile bubbler was 65° C.

The gas path was switched so that the nitrogen gas entered into the quartz tube directly not through another bubbling device, a nitrogen-containing supported carbon catalyst sample was obtained after natural cooling in nitrogen, and was designated as sample 1#.

The mass ratio of the precursor to FNG silica gel was 1.10:1.

The mass ratio of sample 1# to FNG silica gel was 1.12:1.
The photograph of sample 1# is shown in FIG. 1.

Figure 1:
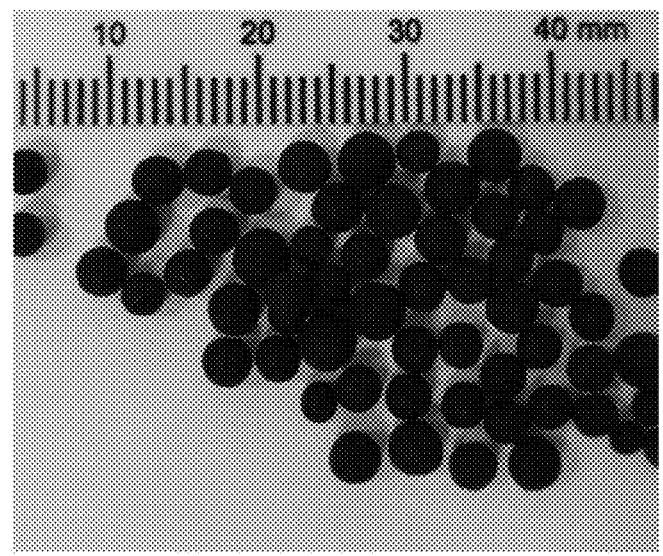
FIG. 1 is a photograph of sample 1#.

As can be seen from FIG. 1, the surface of sample 1# appears black, indicating that the carbon material is sufficiently loaded onto the carrier.

Example 2

The silica gel powder was used as a carrier, the hexamethyldisiloxane was used as an organic silicon source in the step (1), and the pyridine was used as an organic precursor for vapor-depositing in step (2).

(1) 125 mL of silica gel powder was put into a quartz tube, the quartz tube was placed in the tube furnace, a nitrogen gas was introduced as a carrier gas and the temperature was raised to 400° C., and then the gas path was switched so that the nitrogen gas carrying the vaporized hexamethyldisiloxane entered into the quartz tube by way of a bubbling device. The vapor deposition process was performed for 2 hours to graft organosilane.

In vapor deposition, the flow rate of the nitrogen gas was 200 mL/min; the temperature of the hexamethyldisiloxane bubbler was 30° C.

(2) the gas path was switched so that the nitrogen gas entered into the quartz tube directly not through the bubbling device, and the gas path was switched again after the temperature was raised to 750° C. so that the nitrogen gas carrying vaporized pyridine entered into the quartz tube by way of another bubbling device. The chemical vapor deposition process was performed for 2 hours.

In vapor deposition, the flow rate of the nitrogen gas was 250 mL/min; the temperature of the pyridine bubbler was 90° C.

The gas path was switched so that the nitrogen gas entered into the quartz tube directly not through another bubbling device, a nitrogen-containing supported carbon catalyst sample was obtained after natural cooling in nitrogen, and was designated as sample $2^\#$.

The mass ratio of the precursor to the silica gel pellets was 1.08:1.

The mass ratio of sample $2^\#$ to the silica gel pellets was 1.17:1.

Figure 2:
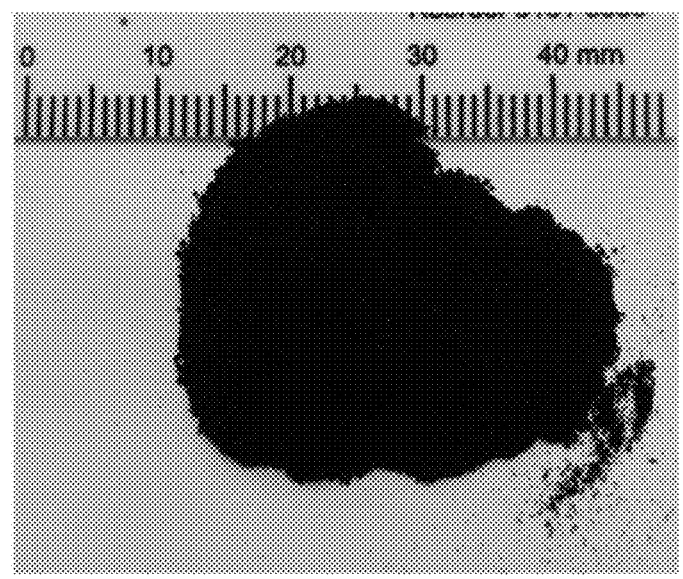
FIG. 2 is a photograph of sample 2#.

The photograph of sample $2^\#$ is shown in FIG. 2.

As can be seen from FIG. 2, the surface of sample $2^\#$ appears black, indicating that the carbon material is sufficiently loaded onto the carrier.

Example 3

The silica gel pellets that washed with hydrochloric acid having a mass concentration of 20% were used as a carrier, the trimethylchlorosilane was used as an organic silicone source in step (1), and the triphenylphosphine was used as an organic precursor for vapor-depositing in step (2).

(1) 65 mL of silica gel pellets were put into a quartz tube, the quartz tube was placed in the tube furnace, an argon gas was introduced as a carrier gas and the temperature was raised to 400° C., and then the gas path was switched so that the argon gas carrying the vaporized trimethylchlorosilane entered into the quartz tube by way of a bubbling device. The vapor deposition process was performed for 2 hours to graft organosilane.

In vapor deposition, the flow rate of the argon gas was 100 mL/min; the temperature of the trimethylchlorosilane bubbler was 30° C.

(2) the gas path was switched so that the argon gas entered into the quartz tube directly not through the bubbling device, and the gas path was switched again after the temperature was raised to 800° C. so that the argon gas carrying vaporized triphenylphosphine entered into the quartz tube by way of another bubbling device. The chemical vapor deposition process was performed for 4 hours.

In vapor deposition, the flow rate of the argon gas was 100 mL/min; the temperature of the triphenylphosphine bubbler was 280° C.

The gas path was switched so that the argon gas entered into the quartz tube directly not through another bubbling device, a phosphorus-containing supported carbon catalyst sample was obtained after natural cooling in argon, and was designated as sample $3^\#$.

The mass ratio of the precursor to the silica gel pellets was 1.10:1.

The mass ratio of sample $3^\#$ to the silica gel pellets was 1.06:1.

The appearance of sample $3^\#$ is similar to that of sample $1^\#$, and the surface of sample $3^\#$ appears black, indicating that the carbon material is sufficiently loaded onto the carrier.

Example 4

The silica gel pellets that washed with hydrochloric acid having a mass concentration of 20% were used as a carrier, the phenyltrichlorosilane was used as an organic silicone source in step (1), and the triphenylboron was used as an organic precursor for vapor-depositing in step (2).

(1) 65 mL of silica gel pellets were put into a quartz tube, the quartz tube was placed in the tube furnace, a nitrogen gas was introduced as a carrier gas and the temperature was raised to 400° C., and then the gas path was switched so that the nitrogen gas carrying the vaporized phenyltrichlorosilane entered into the quartz tube by way of a bubbling device. The vapor deposition process was performed for 2 hours to graft organosilane.

In vapor deposition, the flow rate of the nitrogen gas was 100 mL/min; the temperature of the phenyltrichlorosilane bubbler was 120° C.

(2) the gas path was switched so that the nitrogen gas entered into the quartz tube directly not through the bubbling device, and the gas path was switched again after the temperature was raised to 750° C. so that the nitrogen gas carrying vaporized triphenylboron entered into the quartz tube by way of another bubbling device. The chemical vapor deposition process was performed for 2 hours.

In vapor deposition, the flow rate of the nitrogen gas was 100 mL/min; the temperature of the triphenylboron bubbler was 280° C.

The gas path was switched so that the nitrogen gas entered into the quartz tube directly not through another bubbling device, a boron-containing supported carbon catalyst sample was obtained after natural cooling in nitrogen, and was designated as sample $4^\#$.

The mass ratio of the precursor to the silica gel pellets was 1.06:1.

The mass ratio of sample $4^\#$ to the silica gel pellets was 1.07:1.

The appearance of sample $4^\#$ is similar to that of sample $1^\#$, and the surface of sample $4^\#$ appears black, indicating that the carbon material is sufficiently loaded onto the carrier.

Example 5

The silica gel pellets that washed with hydrochloric acid having a mass concentration of 20% were used as a carrier, the dichlorodimethylsilane was used as an organic silicone source in step (1), and the thiophene was used as an organic precursor for vapor-depositing in step (2).

(1) 65 mL of silica gel pellets were put into a quartz tube, the quartz tube was placed in the tube furnace, a nitrogen gas was introduced as a carrier gas and the temperature was raised to 400° C., and then the gas path was switched so that the nitrogen gas carrying the vaporized dichlorodimethylsilane entered into the quartz tube by way of a bubbling device. The vapor deposition process was performed for 2 hours to graft organosilane.

In vapor deposition, the flow rate of the nitrogen gas was 100 mL/min; the temperature of the dichlorodimethylsilane bubbler was 20° C.

(2) the gas path was switched so that the nitrogen gas entered into the quartz tube directly not through the bubbling device, the temperature was raised to 700° C. and then the thiophene was input into the quartz tube by charging pump. The chemical vapor deposition process was performed for 0.2 hours.

In vapor deposition, the flow rate of the nitrogen was 100 mL/min; the flow rate of thiophene was 0.25 mL/min.

The sulfur-containing supported carbon catalyst sample was obtained after natural cooling in nitrogen, and was designated as sample 5#.

The mass ratio of the precursor to the silica gel pellets was 1.10:1.

The mass ratio of sample 5# to the silica gel pellets was 1.06:1.

The appearance of sample 5# is similar to that of sample 1#, and the surface of sample 5# appears black, indicating that the carbon material is sufficiently loaded onto the carrier.

Example 6

The silica gel pellets that washed with hydrochloric acid having a mass concentration of 20% were used as a carrier, the dimethyldimethoxysilane was used as an organic silicone source in step (1), and the phenol was used as an organic precursor for vapor-depositing in step (2).

(1) 65 mL of silica gel pellets were put into a quartz tube, the quartz tube was placed in the tube furnace, a nitrogen gas was introduced as a carrier gas and the temperature was raised to 400° C., and then the gas path was switched so that the nitrogen gas carrying the vaporized dichlorodimethylsilane entered into the quartz tube by way of a bubbling device. The vapor deposition process was performed for 2 hours to graft organosilane.

In vapor deposition, the flow rate of the nitrogen gas was 100 mL/min; the temperature of the dimethyldimethoxysilane bubbler was 20° C.

(2) the gas path was switched so that the nitrogen gas entered into the quartz tube directly not through the bubbling device, and the gas path was switched again after the temperature was raised to 800° C. so that the nitrogen gas carrying vaporized phenol entered into the quartz tube by way of another bubbling device. The chemical vapor deposition process was performed for 0.2 hours.

In vapor deposition, the flow rate of the nitrogen gas was 100 mL/min; the temperature of the phenol bubbler was 130° C.

The gas path was switched so that the nitrogen gas entered into the quartz tube directly not through another bubbling device, an oxygen-containing supported carbon catalyst sample was obtained after natural cooling in nitrogen, and was designated as sample 6#.

The mass ratio of the precursor to the silica gel pellets was 1.08:1.

The mass ratio of sample 6# to the silica gel pellets was 1.05:1.

The appearance of sample 6# is similar to that of sample 1#, and the surface of sample 6# appears black, indicating that the carbon material is sufficiently loaded onto the carrier.

Example 7

Performance Test of Catalyst

The samples 1# to 6# were used as catalysts for testing the catalytic performance in the the cracking reaction of 1,2-dichloroethane for the preparation of chloroethylene. The specific steps and conditions were as follows:

1,2-dichloroethane liquid was preheated and vaporized in the evaporator, and then passed to a fixed bed reactor loaded with the catalyst by a constant flow pump. The reactor temperature was 250° C., the gaseous hourly space velocity (GHSV) of 1,2-dichloroethane was 133 $h^{-1}$.

The reaction results show that the conversion rates of 1,2-dichloroethane are each higher than 15%, and the selectivities to chloroethylene are each more than 99% using samples 1# to 6# as catalysts in the cracking reaction of 1,2-dichloroethane for the preparation of chloroethylene.

The conversion rate of 1,2-dichloroethane is 40% and the selectivity to chloroethylene is more than 99% using sample 1# as a typical example.

Comparative Example 1

Other steps and conditions were the same as that in example 1 except that the vapor phase deposition process for grafting organosilane was not included, specifically:

(1) 65 mL of FNG silica gel was put into a quartz tube, the quartz tube was placed in the tube furnace, a nitrogen gas was introduced as a carrier gas and the temperature was raised to 800° C., and then the gas path was switched so that the nitrogen gas carrying the vaporized acetonitrile entered into the quartz tube by way of an acetonitrile bubbler. The vapor deposition process was performed for 2 hours.

The gas path was switched so that the nitrogen gas entered into the quartz tube directly not through the bubbling device, a sample designated as sample D-1# was obtained after natural cooling in nitrogen.

Figure 3:
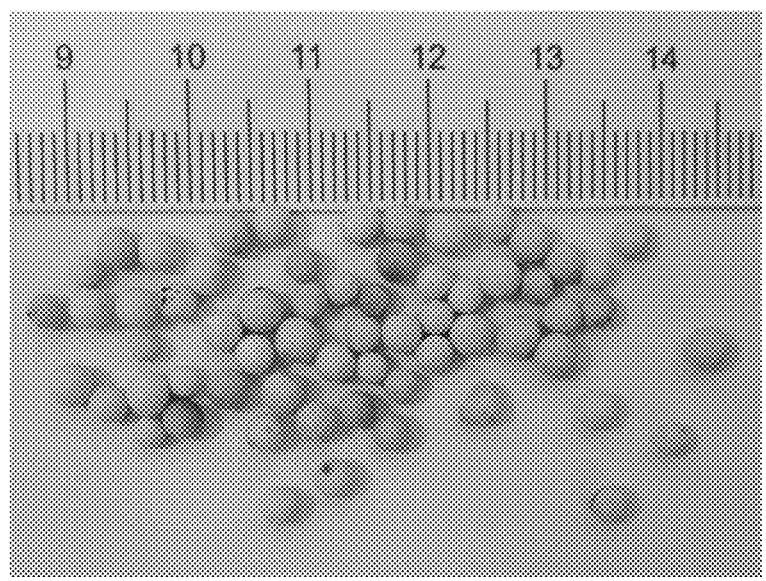
FIG. 3 is a photograph of sample D-1#.

A sample photograph of the sample of D-1# is shown in FIG. 3.

As can be seen from FIG. 3, the surface of sample D-1# appears very light gray, indicating that the amount of carbon material supported on the surface of the FNG silica gel is extremely small.

If the silicone source is not grafted in advance, the nitrogen-containing organic materials can hardly be loaded on the silica gel carrier.

The above are only a few embodiments of the present application, and are not intended to limit the present application in any form. Although the present application is disclosed by the preferred embodiments as above, they are however not used to limit the present application. A slight change or modification utilizing the technical content disclosed above made by the person skilled in art, without departing from the technical solution of the present application, is equivalent to the equivalent embodiment, and falls within the scope of the technical solution.

What is claimed is:

1. A method for preparing a supported carbon catalyst, wherein the method comprises:
   Step (1): contacting a gas containing an organic silicon source with a silicon oxide-based material to obtain a precursor;
   Step (2): contacting the precursor with a gas containing an organic carbon source to obtain the supported carbon catalyst, wherein the precursor obtained in step (1) contacts with the gas containing the organic carbon source at a contact temperature in a range from 500° C. to 1000° C. for 0.1 hour to 10 hours.

2. The method according to claim 1, wherein the organic silicon source in the step (1) is at least one selected from the group consisting of a compound with a chemical formula shown in formula I and a compound with a chemical formula shown in formula II:

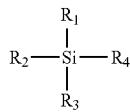

formula I wherein $R_1$, $R_2$, $R_3$ and $R_4$ are each independently selected from the group consisting of hydrogen, a $C_1$ to $C_{12}$ hydrocarbyl group, a $C_1$ to $C_{12}$ substituted hydrocarbyl group, a $C_1$ to $C_5$ hydrocarbyloxy group, a $C_1$ to $C_5$ alkylacyloxy group, halogen and amino; and at least one of $R_1$, $R_2$, $R_3$ and $R_4$ is a $C_1$ to $C_{12}$ hydrocarbyl group or a $C_1$ to $C_{12}$ substituted hydrocarbyl group; and at least one of $R_1$, $R_2$, $R_3$ and $R_4$ is hydrogen, a $C_1$ to $C_5$ hydrocarbyloxy group, a $C_1$ to $C_5$ alkylacyloxy, halogen or amino;

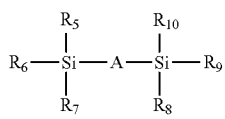

formula II wherein A is O or NH;

$R_5$, $R_6$, $R_7$, $R_8$, $R_9$ and $R_{10}$ are each independently selected from the group consisting of hydrogen, a $C_1$ to $C_{12}$ hydrocarbyl group, a $C_1$ to $C_{12}$ substituted hydrocarbyl group, a $C_1$ to $C_5$ hydrocarbyloxy group, a $C_1$ to $C_5$ alkylacyloxy group, halogen or amino; and at least one of $R_5$, $R_6$ and $R_7$ is a $C_1$ to $C_{12}$ hydrocarbyl group or a $C_1$ to $C_{12}$ substituted hydrocarbyl group; and at least one of $R_8$, $R_9$ and $R_{10}$ is a $C_1$ to $C_{12}$ hydrocarbyl group or a $C_1$ to $C_{12}$ substituted hydrocarbyl group.

3. The method according to claim 2, wherein a substituent is contained in the substituted hydrocarbyl group; the substituent is at least one selected from the group consisting of halogen, amino, epoxyethyl, sulfydryl, cyano, isocyanate group, and ethylenediamine.

4. The method according to claim 1, wherein the organic silicon source in step (1) is least one selected from the group consisting of dichlorodimethylsilane, hexamethyldisiloxane, trimethylchlorosilane, phenyltrichlorosilane and dimethoxydimethylsilane.

5. The method according to claim 1, wherein the gas containing the organic silicon source in step (1) contains or does not contain an inactive gas;

the inactive gas is at least one selected from the group consisting of nitrogen, argon gas and helium gas.

6. The method according to claim 1, wherein the silicon oxide-based material in step (1) is porous silicon dioxide.

7. The method according to claim 1, wherein the gas containing the organic silicon source in step (1) contacts with the silicon oxide-based material at a contact temperature in a range from 100° C. to 500° C. for 0.1 hour to 10 hours.

8. The method according to claim 1, wherein the gas containing the organic silicon source in step (1) contacts with the silicon oxide-based material at a contact temperature in a range from 200° C. to 450° C. for 0.2 hour to 4 hours.

9. The method according to claim 1, wherein the mass percentage of the silicon oxide-based material in the precursor is in a range from 80 wt % to 98 wt %.

10. The method according to claim 1, wherein the mass percentage of the silicon oxide-based material in the precursor is in a range from 90 wt % to 97 wt %.

11. The method according to claim 1, wherein the organic carbon source in the step (1) is at least one of a $C_1$ to $C_{18}$ organic compound;

the organic compound contains at least one selected from the group consisting of nitrogen, oxygen, boron, phosphorus, and sulfur.

12. The method according to claim 1, wherein the organic carbon source in step (2) is at least one selected from the group consisting of nitrile compounds, pyridine compounds, organic phosphine compounds, organoboron compounds, thiophene compounds, phenol compounds, and alcohol compounds.

13. The method according to claim 1, wherein the gas containing the organic carbon source in step (2) contains an inactive gas;

the inactive gas is at least one selected from the group consisting of nitrogen, argon gas and helium gas.

14. The method according to claim 1, wherein the precursor in step (2) contacts with the gas containing the organic carbon source at a contact temperature in a range from 600° C. to 900° C. for 0.1 hour to 4 hours.

15. The method according to claim 1, wherein the mass percentage of the silicon oxide-based material in the supported carbon catalyst is in a range from 60 wt % to 95 wt %.

16. The method according to claim 1, wherein the mass percentage of the silicon oxide-based material in the supported carbon catalyst is in a range from 75 wt % to 93 wt %.

* * * * *